(12) United States Patent
Miyagawa et al.

(10) Patent No.: US 10,371,615 B2
(45) Date of Patent: Aug. 6, 2019

(54) PARTICULATE MATTER DETECTION SENSOR

(71) Applicant: DENSO CORPORATION, Kariya, Aichi-pref. (JP)

(72) Inventors: Go Miyagawa, Kariya (JP); Masayuki Tamura, Kariya (JP)

(73) Assignee: DENSO CORPORATION, Kariya (JP)

(*) Notice: Subject to any disclaimer, the term of this patent is extended or adjusted under 35 U.S.C. 154(b) by 128 days.

(21) Appl. No.: 15/520,206

(22) PCT Filed: Oct. 8, 2015

(86) PCT No.: PCT/JP2015/078567
§ 371 (c)(1),
(2) Date: Apr. 19, 2017

(87) PCT Pub. No.: WO2016/063737
PCT Pub. Date: Apr. 28, 2016

(65) Prior Publication Data
US 2017/0315042 A1    Nov. 2, 2017

(30) Foreign Application Priority Data
Oct. 20, 2014  (JP) .................................. 2014-213510

(51) Int. Cl.
*G01M 15/10*    (2006.01)
*G01N 15/06*    (2006.01)
(Continued)

(52) U.S. Cl.
CPC ..... *G01N 15/0618* (2013.01); *F02D 41/1444* (2013.01); *G01N 15/06* (2013.01);
(Continued)

(58) Field of Classification Search
USPC .......................................... 73/114.69, 114.71
See application file for complete search history.

(56) References Cited

U.S. PATENT DOCUMENTS

| 2008/0024111 A1 | 1/2008 | Dorfmueller et al. |
| 2008/0232956 A1 | 9/2008 | Baldauf et al. |

(Continued)

FOREIGN PATENT DOCUMENTS

| JP | 2012-078130 | 4/2012 |
| JP | 2014-032063 | 2/2014 |

OTHER PUBLICATIONS

English translation of International Search Report issued in PCT/JP2015/078567 dated Dec. 22, 2015 (2 pages).

*Primary Examiner* — Eric S. McCall
(74) *Attorney, Agent, or Firm* — Nixon & Vanderhye P.C.

(57) ABSTRACT

A particulate matter detection sensor has an accumulation section for accumulating a part of particulate matter particles contained in exhaust gas emitted from an internal combustion engine, and a pair of a first detection electrode and a second detection electrode formed on the accumulation section. The second detection electrode is formed separated from the first detection electrode. The first detection electrode has projecting parts which project toward the second detection electrode. Because a separation between the first and second detection electrodes is locally reduced at the projecting parts, the projecting parts attract and accumulate more particulate matter, and this structure makes it possible to allow the particulate matter detection sensor to have improved detection sensitivity.

9 Claims, 5 Drawing Sheets

(51) Int. Cl.
  *G01N 27/04* (2006.01)
  *F02D 41/14* (2006.01)
  *F01N 11/00* (2006.01)
  *G01N 15/00* (2006.01)

(52) U.S. Cl.
  CPC ......... *G01N 15/0656* (2013.01); *G01N 27/04* (2013.01); *F01N 11/00* (2013.01); *F01N 2550/04* (2013.01); *F01N 2560/05* (2013.01); *G01N 2015/0046* (2013.01); *Y02T 10/47* (2013.01)

(56) References Cited

U.S. PATENT DOCUMENTS

| | | | |
|---|---|---|---|
| 2010/0008773 A1 | 1/2010 | Baldauf et al. | |
| 2011/0203348 A1 | 8/2011 | Hedayat et al. | |
| 2011/0259079 A1* | 10/2011 | Maeda | G01N 15/0656 73/23.33 |
| 2011/0314796 A1* | 12/2011 | Nakamura | F01N 9/002 60/276 |
| 2012/0031169 A1* | 2/2012 | Sakamoto | F02D 41/1466 73/25.05 |
| 2012/0034569 A1* | 2/2012 | Sakamoto | G01N 15/0656 431/76 |
| 2012/0085146 A1* | 4/2012 | Maeda | G01N 27/043 73/23.31 |
| 2012/0103057 A1* | 5/2012 | Kimata | G01N 15/0656 73/23.33 |
| 2012/0103058 A1* | 5/2012 | Maeda | G01N 15/0656 73/23.33 |
| 2012/0103059 A1* | 5/2012 | Kimata | F01N 11/00 73/23.33 |
| 2012/0151992 A1* | 6/2012 | Harada | G01N 15/0656 73/23.33 |
| 2012/0266646 A1* | 10/2012 | Maeda | F04D 1/1466 73/1.06 |
| 2013/0019653 A1* | 1/2013 | Nakata | F02D 41/1466 73/23.33 |
| 2013/0283886 A1* | 10/2013 | Teranishi | G01N 33/0047 73/23.31 |
| 2016/0320285 A1* | 11/2016 | Weber | G01N 15/0656 |
| 2017/0131185 A1* | 5/2017 | Koike | G01N 27/04 |
| 2017/0322134 A1* | 11/2017 | Koike | G01N 15/06 |
| 2018/0052091 A1* | 2/2018 | Zhang | F01N 11/007 |
| 2018/0266934 A1* | 9/2018 | Mouri | G01M 15/102 |
| 2018/0266936 A1* | 9/2018 | Yamamoto | G01N 15/1031 |

\* cited by examiner

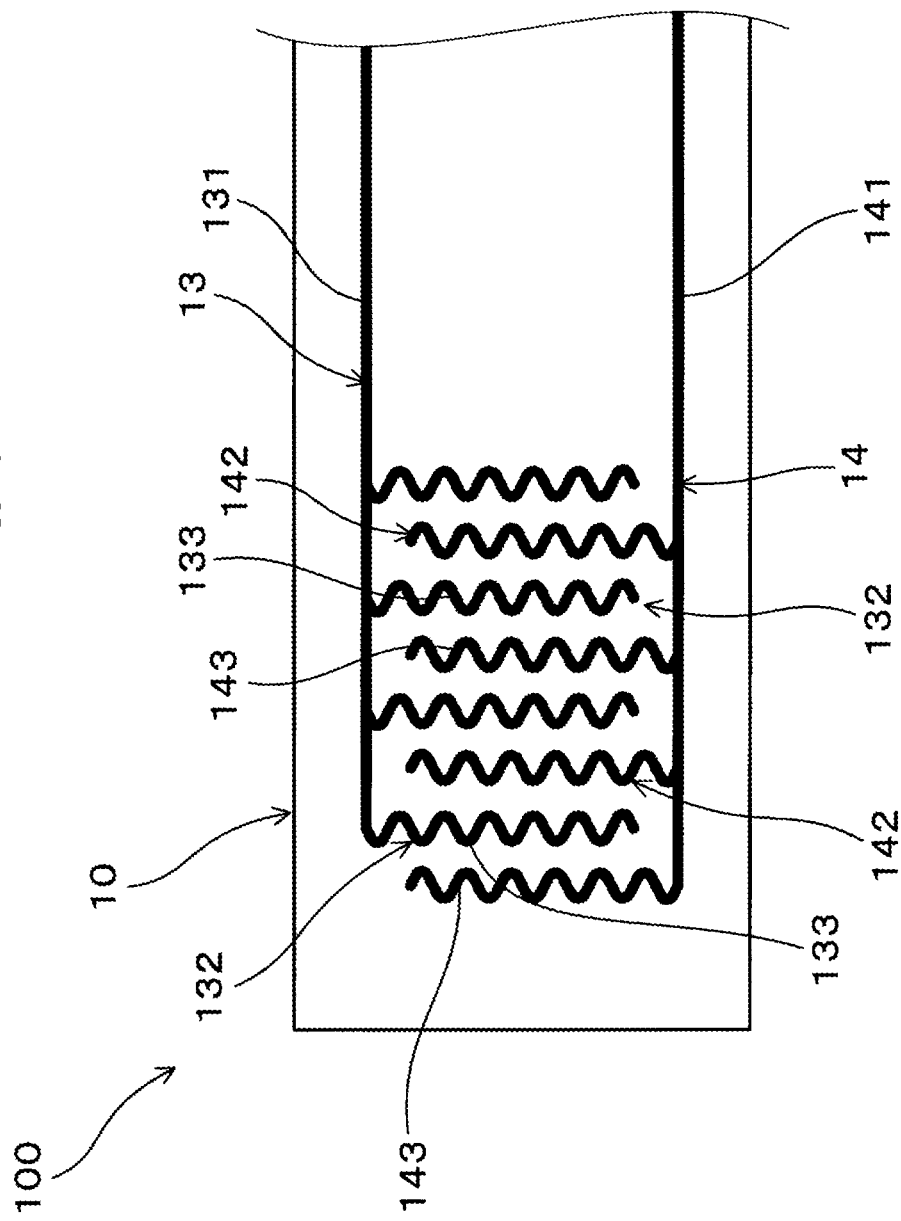

PARTICULATE MATTER DETECTION SENSOR

This application is the U.S. national phase of International Application No. PCT/JP2015/078567 filed Oct. 8, 2015 which designated the U.S. and claims priority to JP Patent Application No. 2014-213510 filed Oct. 20, 2014, the entire contents of each of which are hereby incorporated by reference.

TECHNICAL FIELD

The present invention relates to particulate matter detection sensors having a structure for improving their detection sensitivity.

BACKGROUND ART

An exhaust gas purification device is arranged in an exhaust gas pipe of an internal combustion engine. The exhaust gas purification device captures and collects particulate matter contained in exhaust gas emitted from the internal combustion engine. The exhaust gas purification device has a particulate matter detection device. The particulate matter detection device is equipped with a particulate matter detection sensor for detecting an amount of particulate matter contained in exhaust gas. A failure detection of the exhaust gas purification device is executed on the basis of detection information provided from the particulate matter detection device.

For example, there is a particulate matter detection sensor to be used in an exhaust gas purification device disclosed in a patent document 1. The particulate matter detection sensor disclosed in the patent document 1 has a structure in which electrode layers and insulation layers are alternately stacked, end surfaces of the electrode layers are exposed to outside, and multiple detection electrodes are formed so that the multiple detection electrodes are formed in parallel to each other.

CITATION LIST

Patent Literature

[Patent document 1] Japanese patent laid open publication No. JP 2012-78130.

SUMMARY OF INVENTION

Technical Problem

However, the particulate matter detection sensor disclosed in the patent document 1 has the following drawback. The particulate matter detection sensor disclosed in the patent document 1 has the structure in which the multiple detection electrodes are formed parallel to each other. A uniform electric field is generated between the detection electrodes when a voltage is applied to the detection electrodes so as to attract particulate matter contained in exhaust gas. Because particulate matter is randomly collected in the generated electric field on the particulate matter detection sensor, and accumulates and is adhered between the detection electrodes, it requires a period of time until a conductive path made of particulate matter is formed between the detection electrodes. This reduces the detection sensitivity of the particulate matter detection sensor.

The present invention has been made in consideration of the foregoing circumstances, and it is an object of the present invention to provide a particulate matter detection sensor having a structure for improving its detection sensitivity.

Solution to Problem

In accordance with an exemplary embodiment of the present invention, there is provided a particulate matter detection sensor having an accumulation section, and a detection electrode. The accumulation section accumulates a part of particulate matter contained in exhaust gas emitted from an internal combustion engine. The detection electrode is composed of a pair of a first detection electrode and a second detection electrode formed on the accumulation section. The second detection electrode is formed separated from the first detection electrode on the accumulation section. The projecting parts are formed on at least one of the first detection electrode and the second detection electrode. The projecting parts formed on at least one of the first detection electrode and the second detection electrode project toward the other detection electrode. A separation or separation between the first detection electrode and the second detection electrode is locally reduced at the projecting parts. Further, equipotential lines of electric field at the projecting parts have a high density when compared with equipotential lines of the electric field at an area excepting the projecting parts between the first detection electrode and the second detection electrode.

Advantageous Effects of Invention

The projecting parts are formed on the pair of the first and second detection electrodes in the particulate matter detection sensor. This structure makes it possible to increase its detection sensitivity for detecting particulate matter. That is, the formation of the projecting parts allows the separation between the first detection electrode and the second detection electrode to be locally reduced at the projecting parts. Accordingly, a density of electric field generated between the first detection electrode and the second detection electrode increases at the projecting parts, and a strong electric field is generated at the projecting parts when compared with an electrode field generated in a section, between the first detection electrode and the second detection electrode, excepting the projecting parts, and the projecting parts having the high electric field attract preferentially particulate matter.

In addition, when particulate matter captured by and accumulated in the projecting parts has a conductivity, because the projecting parts and the particulate matter have substantially the same electric field intensity, the particulate matter accumulated on the accumulation section has the function of the projecting parts and therefore further attracts particulate matter contained in exhaust gas. This makes it possible to selectively adhere particulate matter to the projecting parts and speedily accumulate particulate matter between the first detection electrode and the second detection electrode on the accumulation section so as to rapidly form electrical conduction between the first detection electrode and the second detection electrode formed on the accumulation section. Accordingly, this improved structure of the particulate matter detection sensor makes it possible to increase detection sensitivity for detecting particulate matter contained in exhaust gas.

BRIEF DESCRIPTION OF DRAWINGS

FIG. 6 is a view explaining a particulate matter detection sensor according to a fourth exemplary embodiment.

DESCRIPTION OF EMBODIMENTS

In the particulate matter detection sensor according to the present invention, the projecting parts are formed between the first detection electrode and the second detection electrode. It is preferable to arrange the first detection electrode and the second detection electrode to face each other. This structure makes it possible to form a strong electric field by the projecting parts in which the first detection electrode and the second detection electrode face each other. Accordingly, it is possible for the projecting parts to attract a large amount of particulate matter, and this structure makes it possible to improve the detection sensitivity of the particulate matter detection sensor.

Further, it is preferable for at least one of the first detection electrode and the second detection electrode to have the projecting parts. This structure allows each of the projecting parts to attract and stably collect particulate matter. Accordingly, it is possible for the particulate matter detection sensor having the structure to provide an improved detection sensitivity.

Still further, in the particulate matter detection sensor having the structure previously described, detection electrode layers and insulation layers are alternately stacked. The insulation layers have electrical insulation properties. It is preferable to form insulation projecting parts in one of the insulation layers with which the detection layer having the projecting parts is sandwiched, and to form insulation depressed parts in the other insulation layers with which the detection layer having the projecting parts is sandwiched, wherein the insulation projecting parts and the insulation depressed parts are faced from each other. This structure makes it possible to provide the effect to allow the detection electrodes having the projecting parts to be easily formed.

Still further, in a production process in which the detection electrode layers and the insulation layers are alternately stacked and bonded together to produce the particulate matter detection sensor, it is preferable for the detection electrode to have the projecting parts formed in a curved shape along the insulation projecting parts and the insulation depressed parts, by pressing in a stack direction of the insulation layers and the detection layers, wherein each detection layer is sandwiched by the corresponding insulation layers, and the insulation projecting parts and the insulation depressed parts face each other. This structure makes it possible to easily form the projecting parts in the detection electrode along the pair of the insulation layers, and to easily produce the particulate matter detection sensor with superior detection sensitivity for detecting the presence of particulate matter.

EXEMPLARY EMBODIMENTS

First Exemplary Embodiment

Figure 1:
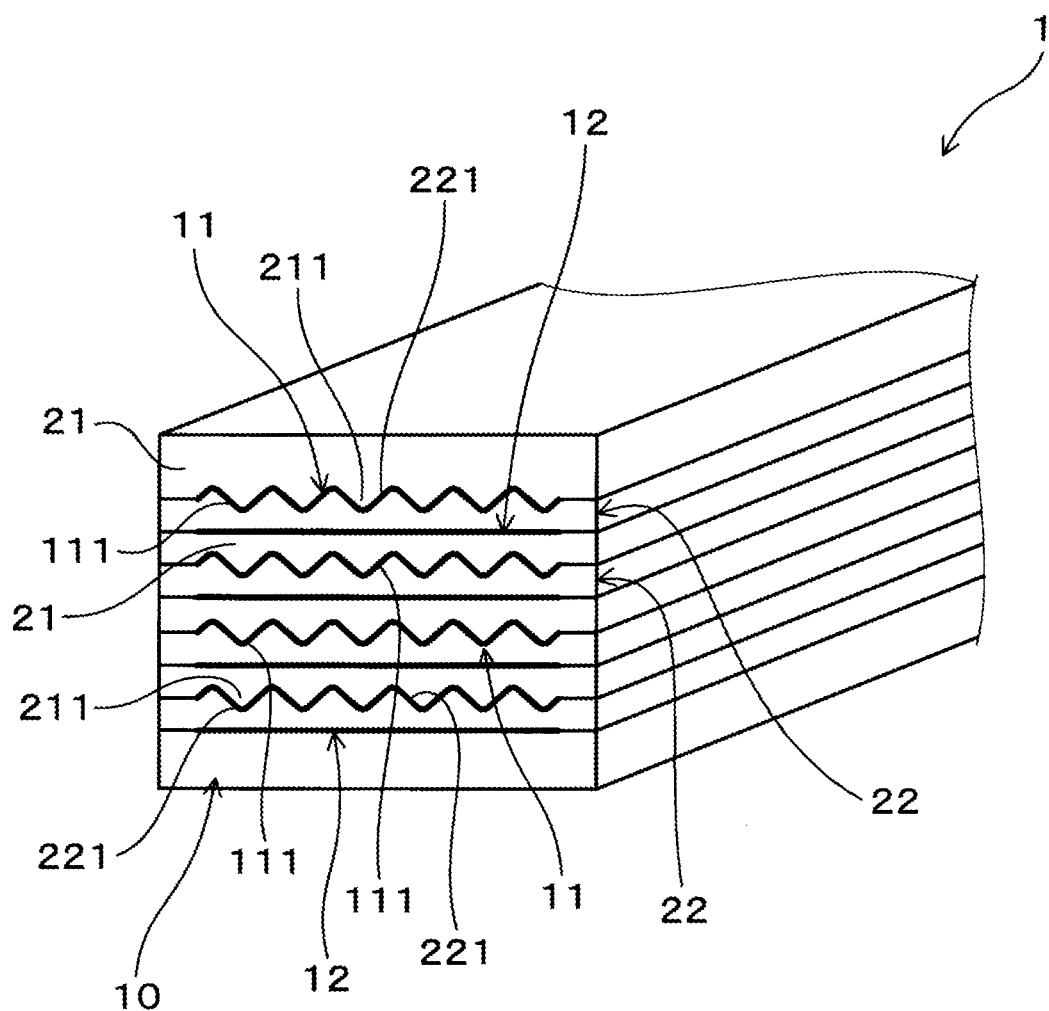
FIG. 1 is a view explaining a particulate matter detection sensor according to a first exemplary embodiment.

A description will be given of the particulate matter detection sensor 1 according to the first exemplary embodiment with reference to FIG. 1 to FIG. 3. As shown in FIG. 1, the particulate matter detection sensor 1 according to the first exemplary embodiment has an accumulation section 10 and first detection electrodes 11 and second detection electrodes 12, in which the first detection electrode 11 and the second detection electrode 12 form a pair. That is, multiple pairs of the first detection electrode 11 and the second detection electrode 12 are formed on the accumulation section 10. The accumulation section 10 collects a part of particulate matter (P) particles contained in exhaust gas emitted from an internal combustion engine. The collected particulate matter P accumulates on the accumulation section 10. The second detection electrode 12 is arranged separated from the first detection electrode 11 The projecting parts 111, which project toward the second detection electrode 12, are formed in the first detection electrode 11. A separation or gap between the first detection electrode 11 and the second detection electrode 12 is locally reduced at each of the projecting parts 111.

Hereinafter, a description will now be given of the particulate matter detection sensor 1 according to the first exemplary embodiment in detail. The particulate matter detection sensor 1 according to the first exemplary embodiment detects particulate matter P contained in exhaust gas emitted from an internal combustion engine and passing through an exhaust gas, which are mounted on a vehicle. A failure detection process of the exhaust gas purification device is performed on the basis of information obtained from the particulate matter detection sensor 1. The particulate matter detection sensor 1 is arranged in the inside of the exhaust gas pipe so that the particulate matter detection sensor 1 projects into the inside of the exhaust gas pipe. A front end side of the particulate matter detection sensor 1 is arranged inside of the exhaust gas pipe along an axial direction of the particulate matter detection sensor 1. A distal end side of the particulate matter detection sensor 1 is opposite to the front end side of the particulate matter detection sensor 1.

Figure 2:
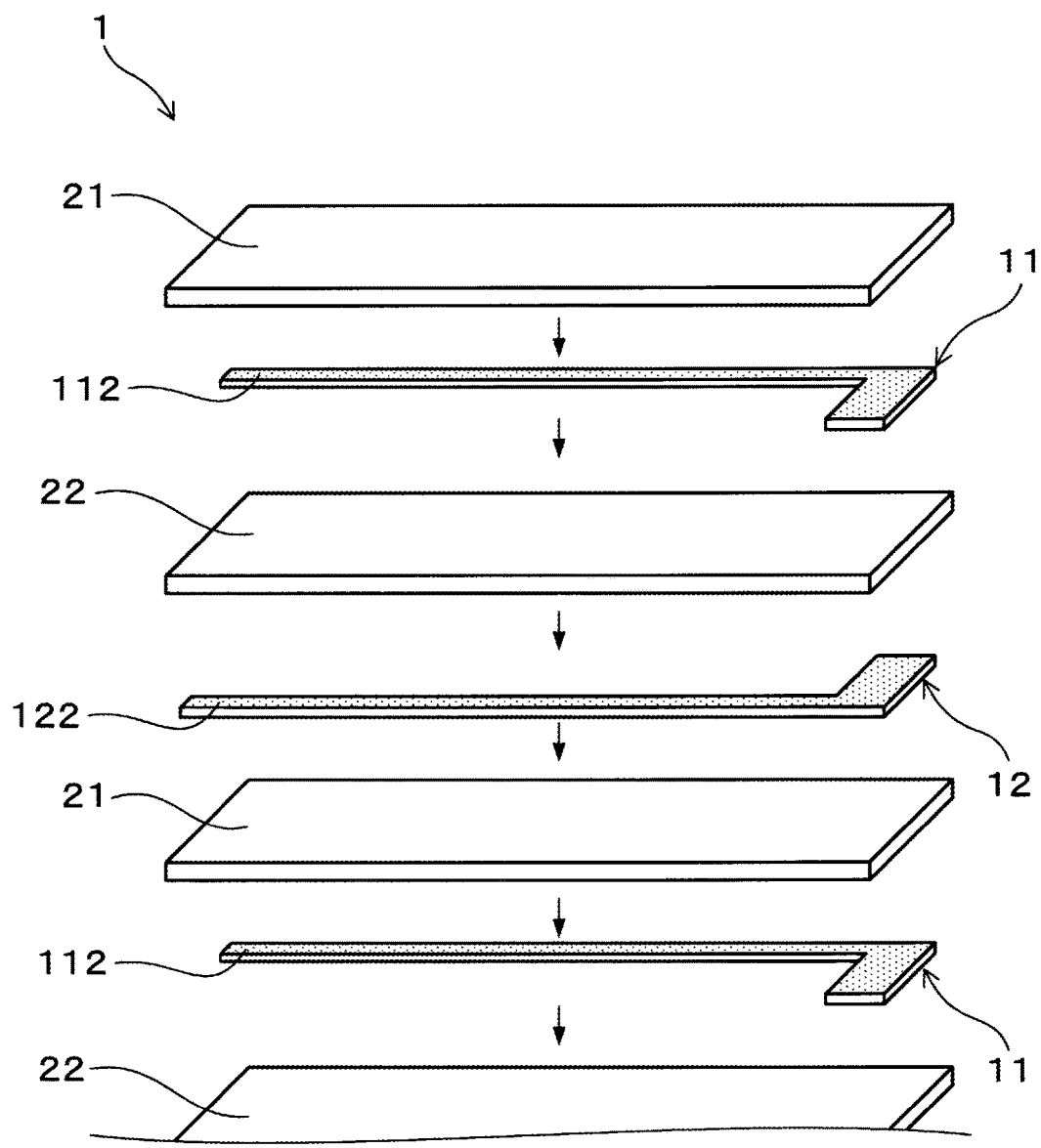
FIG. 2 is a view explaining a structure of the particulate matter detection sensor according to the first exemplary embodiment.
Figure 3:
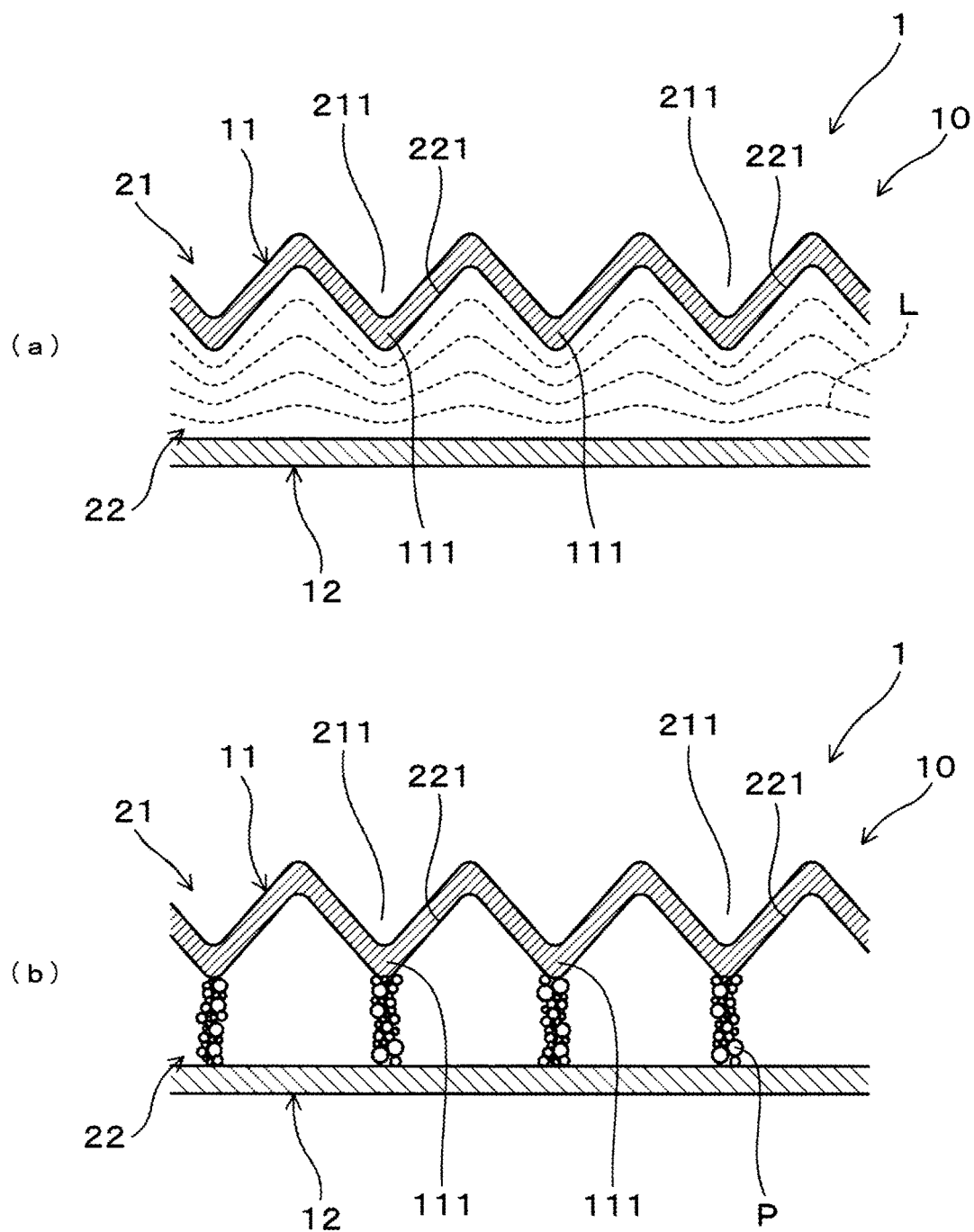
FIG. 3(a) is a view explaining equipotential lines formed in the particulate matter detection sensor according to the first exemplary embodiment, and (b) is a view explaining particulate matter which has been adhered and has accumulated in the particulate matter detection sensor according to the first exemplary embodiment.

As shown in FIG. 1 and FIG. 2, the particulate matter detection sensor 1 has the accumulation section 10, the multiple first detection electrodes 11 and the multiple second detection electrodes 12. Particulate matter P contained in exhaust gas accumulate on the accumulation section 10, and the first detection electrode 11 is separated from the second detection electrode 12. The particulate matter detection sensor 1 has the structure in which the nine insulation members 21 and 22 made of insulation material and the eight detection electrodes 11, 12 are alternately stacked to form a stick-like shape sensor. The accumulation section 10 is formed on a front end surface of the particulate matter detection sensor 1, on which the first detection electrodes 11 and the second detection electrodes 12 are exposed.

The eight detection electrodes 11 and 12 composed of the first detection electrodes and the second detection electrodes are alternately arranged and made of copper. The first detection electrodes 11 are used as a positive electrode, and the second detection electrodes 12 are used as a negative electrode. The first detection electrode 11 and the second detection electrodes 12 are arranged adjacently from each other. Each of the first detection electrodes 11 has the projecting parts 111 which project toward the corresponding second detection electrode 12, respectively. In the first exemplary embodiment, when viewed from the front end side of the particulate matter detection sensor 1, the projection part 111 in the first detection electrode 11 has a mountain shape structure, a mountain-like shape structure, a triangle shape structure, or a triangle-like shape structure.

The second detection electrode 12 has a flat-like shape structure. Lead sections 112 and 122 are connected to the first detection electrode 11 and the second detection electrode 12, respectively and formed extending to the distal end side of the particulate matter detection sensor 1. The minimum separation between the projecting part 111 in the first detection electrode 11 and the b second detection electrode 12 is 10 µm.

The insulation members 21 and 22 are made of ceramic material such as alumina, zirconia, magnesia, beryllia, etc. and formed in a plate shape. In the first exemplary embodiment, a pair of the insulation members 21, 22 have a shape which corresponds to the shape of the first detection electrode 11. A plurality of the insulation projecting parts 211 are formed on a surface of the insulation member 21 in a pair of the insulation members 21 and 22, with which the first detection electrode 11 is sandwiched. The surface of the insulation member 21 faces the surface of the first detection electrode 11 on which the insulation projecting parts 211 are formed. The insulation projecting parts 211 project toward the insulation member 22. In addition, a plurality of the insulation depressed parts 221 are formed in the surface of the insulation member 22, which faces the first detection electrode 11 so that the insulation depressed parts 221 correspond to the insulation projecting parts 211 formed in the insulation member 21.

The first detection electrode 11 having a thin plate shape is arranged between the insulation members 21 and 22. The first detection electrode 11, the insulation members 21 and 22 are pressed in the stack direction of the insulation members 21, 22. This process makes it possible to deform the first detection electrode 11 to be fitted with the shape of the insulation projecting parts 211 and the insulation depressed parts 221. That is, the first detection electrode 11 is curved along the shape of the insulation projecting parts 211 and the insulation depressed parts 221, and the projecting part 111 are formed in the first detection electrode 11.

As shown in FIG. 3(b), when the particulate matter P is accumulated on the accumulation section 10, the particulate matter P accumulated on the accumulation section 10 allows the electrical conduction to occur between the first detection electrode 11 and the second detection electrode 12, and as a result, reduces an electrical resistance between the first detection electrode 11 and the second detection electrode 12. An amount of a current, which represents an electrical signal, flowing between the first detection electrode 11 and the second detection electrode 12 varies due to the variation of the electrical resistance between the first detection electrode 11 and the second detection electrode 12. The particulate matter detection sensor 1 outputs a current value which varies the variation of the current flowing between the first detection electrode 11 and the second detection electrode 12. That is, the current value as the output of the particulate matter detection sensor 1 varies on the basis of the accumulation amount of particulate matter P accumulated on the accumulation section 10, and provides information regarding the amount of particulate matter P accumulated on the accumulation section 10. It is accordingly possible to detect the amount of particulate matter P accumulated on the accumulation section 10 on the basis of the current value as the output of the particulate matter detection sensor 1. In the particulate matter detection sensor 1 according to the first exemplary embodiment, a particulate matter amount detection section detects a current, and outputs the detected current value to a control unit having a shunt resistance. The control unit outputs a voltage value which is obtained by multiplying the current value and the shunt resistance together. This voltage value is the output of the particulate matter detection sensor 1.

Next, a description will now be given of the explanation of the behavior and effects of the particulate matter detection sensor 1 according to the first exemplary embodiment.

In the particulate matter detection sensor 1 according to the first exemplary embodiment, the projecting parts 111 are formed on the first detection electrode 11 in a pair of the first detection electrode 11 and the second detection electrode 12. The formation of the projecting parts 111 makes it possible to improve the detection sensitivity of the particulate matter detection sensor 1. That is, as shown in FIG. 3(a), the formation of the projecting parts 111 allows the separation between the first detection electrode 11 and the second detection electrode 12 to be drastically reduced at the projecting parts 111. This makes it possible to provide equipotential lines L having a high density between the first detection electrode 11 and the second detection electrode 12, and generates a strong electric field at the projecting parts 111 when compared with the parts other than the projecting parts 111.

As shown in FIG. 3(b), particulate matter P is strongly attracted to and adhered on the projecting parts 111. When particulate matter P adhered on the projecting parts 111 has conductivity, because the projecting parts 111 and the particulate matter P accumulated and adhered on the projecting parts 111 have the same electrical potential, the particulate matter P adhered on the projecting parts 111 function as the projecting parts 111, and as a result, the projecting parts 111 further attract particulate matter P contained in exhaust gas. This makes it possible for the projecting parts 111 to provide selective attraction of particulate matter P, and speedily execute the electrical conduction between the first detection electrode 11 and the second detection electrode 12. This makes it possible to improve the detection sensitivity of the particulate matter detection sensor 1.

Further, because the first detection electrode 11 has a plurality of the projecting parts 111, the projecting parts 111 attract and accumulate particulate matter P. This makes it possible to provide the stable collection of particulate matter P and to more improve the detection sensitivity of the particulate matter detection sensor 1.

Still further, the minimum separation between the first detection electrode 11 and the second detection electrode 12 is within a range of not less than 1 µm and not more than 50 µm. This structure makes it possible to provide the improved detection sensitivity of the particulate matter detection sensor 1 while maintaining the productivity of the particulate matter detection sensor 1. In particular, it is preferable for the separation between the first detection electrode 11 and the second detection electrode 12 to have the minimum value, as small as possible, of not less than 1 µm. The more the minimum separation between the first detection electrode 11 and the second detection electrode 12 reduces, the more the conductivity between the first detection electrode 11 and the second detection electrode 12 rapidly occurs. This makes it possible to improve the detection sensitivity of the particulate matter detection sensor 1.

Still further, the particulate matter detection sensor 1 is produced to have a structure in which the multiple first detection electrodes 11, the multiple second detection electrodes 12 and the multiple insulation members 21, 22 are alternately stacked, and each first detection electrode 11 is sandwiched by the first insulation member 21 and the second insulation member 22. The insulation projecting parts 211 are formed on he insulation member 21 to project toward the second insulation member 22. The insulation depressed parts 221 are formed o the second insulation member 22 to face the insulation projecting parts 211. This structure makes it possible to easily form the projecting parts 111 in the first detection electrode 11.

Further, the multiple detection electrodes 11, 12 and the insulation members 21, 22 are alternately stacked and joined together.

In the production of the particulate matter detection sensor 1, the first detection electrode 11 is sandwiched between the first and second insulation members 21, 22 so that the insulation projecting parts 211 are arranged to face the insulation depressed parts 221. The insulation members 21, 22 and the first detection electrode 11 are pressed in the stack direction of the insulation members 21, 22 to deform the first detection electrode 11 along the insulation projecting parts 211 and the insulation depressed parts 221 so as to form the projecting parts 111 in the first detection electrode 11. This process makes it possible to easily form the projecting parts 111 in the first detection electrode 11 by using the insulation members 21, 22. This process makes it possible to provide the particulate matter detection sensor 1 with superior detection sensitivity for detecting particulate matter P.

As previously described, the first exemplary embodiment provides the particulate matter detection sensor 1 capable of detecting particulate matter P with improved detection sensitivity.

Second Exemplary Embodiment

A description will be given of the particulate matter detection sensor 1 according to the second exemplary embodiment with reference to FIG. 4.

Figure 4:
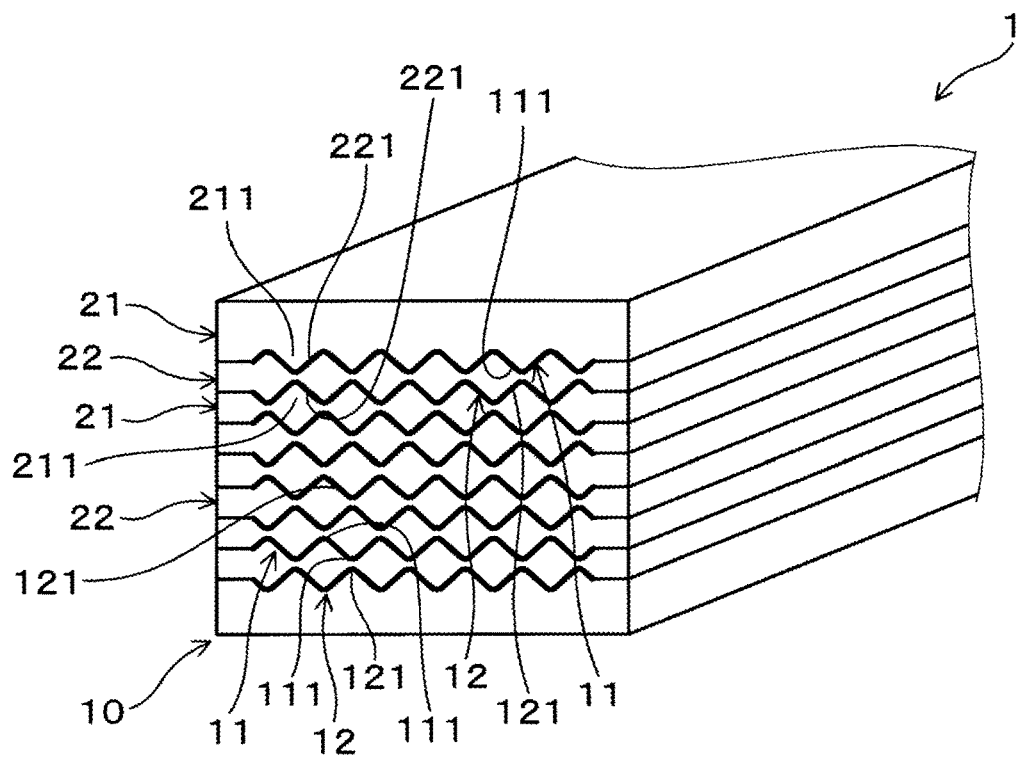
FIG. 4 is a view explaining a particulate matter detection sensor according to a second exemplary embodiment.

As shown in FIG. 4, the particulate matter detection sensor 1 according to the second exemplary embodiment has a structure which is different in part from the structure of the particulate matter detection sensor 1 according to the first exemplary embodiment.

In the structure of the particulate matter detection sensor 1 according to the second exemplary embodiment, the projecting parts 111 and projecting parts 121 are formed on the first detection electrode 11 and the second detection electrode 12, respectively. The first detection electrode 11 has substantially the same structure of the first detection electrode 11 formed in the particulate matter detection sensor 1 according to the second exemplary embodiment. On the other hand, the second detection electrode 12 is formed in the accumulation section 10 so that the second detection electrode 12 and the first detection electrode 11 are arranged in linear symmetry when viewed from the straight line which is perpendicular to the stack direction of the insulation members 21, 22 in the particulate matter detection sensor 1. Accordingly, the projecting parts 111 in the first detection electrode 11 face the projecting parts 121 in the second detection electrode 12, respectively.

Further, the insulation projecting parts 211 and insulation depressed parts 221 are formed on the surfaces of the insulation members 21, 22, respectively, between which the second detection electrode 12 is sandwiched. Those surfaces of the insulation members 21, 22 face the second detection electrode 12. Other components of the particulate matter detection sensor 1 according to the second exemplary embodiment are the same as the particulate matter detection sensor 1 according to the first exemplary embodiment previously described. The same components will be referred with the same reference numbers and characters.

In the structure of the particulate matter detection sensor 1 according to the second exemplary embodiment, the projecting parts 111 and the projecting parts 121 are formed on the first detection electrode 11 and the second detection electrode 12, respectively, so that the projecting parts 111 in the first detection electrode 11 face the projecting parts 121 in the second detection electrode 12. Accordingly, the parts at which the projecting parts 111 face the projecting parts 121, respectively, have a strong electric field intensity, and the parts attract and accumulate particulate matter P contained in exhaust gas. This makes it possible to provide the particulate matter detection sensor 1 having the improved detection sensitivity to detect particulate matter P. The particulate matter detection sensor 1 according to the second exemplary embodiment has the same effects of the particulate matter detection sensor 1 according to the first exemplary embodiment.

Third Exemplary Embodiment

A description will be given of the particulate matter detection sensor 1 according to the third exemplary embodiment with reference to FIG. 5.

Figure 5:
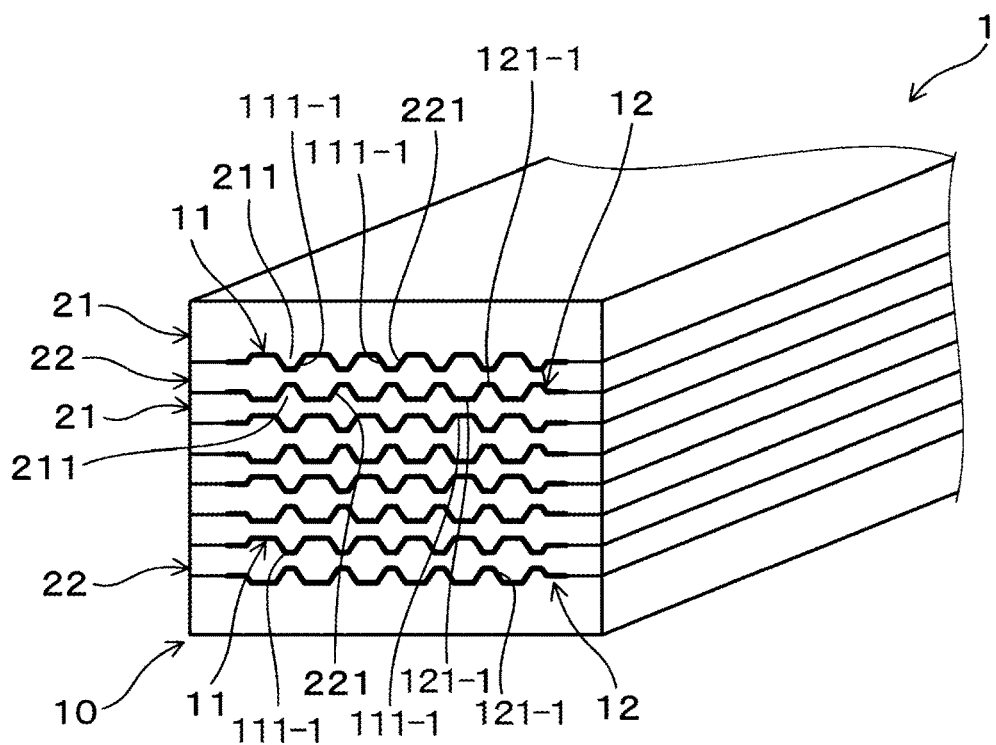
FIG. 5 is a view explaining a particulate matter detection sensor according to a third exemplary embodiment

As shown in FIG. 5, the particulate matter detection sensor 1 according to the third exemplary embodiment has projecting parts capable of attracting particulate matter P, each of which has a structure which is different from the structure of the projecting parts 111 and the projecting parts 121 in the particulate matter detection sensor 1 according to the second exemplary embodiment previously described.

In the structure of the particulate matter detection sensor 1 according to the third exemplary embodiment shown in FIG. 5, multiple projecting parts 111-1 and multiple projecting parts 121-1 are formed on the first detection electrode 11 and the second detection electrode 12, respectively, each of which has a trapezoid shape or a trapezoid-like shape. Other components of the particulate matter detection sensor 1 according to the third exemplary embodiment are the same as the particulate matter detection sensor 1 according to the second exemplary embodiment previously described. The same components will be referred with the same reference numbers and characters.

Fourth Exemplary Embodiment

A description will be given of the particulate matter detection sensor 100 according to the fourth exemplary embodiment with reference to FIG. 6.

As shown in FIG. 6, the particulate matter detection sensor 100 according to the fourth exemplary embodiment has a structure which is different from the structure of the particulate matter detection sensor 1 according to each of the first to third exemplary embodiments previously described.

The particulate matter detection sensor 100 according to the fourth exemplary embodiment has the accumulation section 10 for accumulating particulate matter P contained in exhaust gas, and a pair of first and second detection electrodes 13, 14. The first and second detection electrodes 13, 14 are arranged in the accumulation section 10 to separate from each other by a predetermined separation. The accumulation section 10 has a rectangle-like plate shape and is made of insulation material. The first and second detection electrodes 13, 14 are made of conductive material. The first and second detection electrodes 13, 14 have a plate thin film which is printed on a surface of the accumulation section 10 by a pattern printing process, etc. In a pair of the first and second detection electrodes 13, 14, the first detection electrodes 13 has comb teeth parts 132, and the second detection electrodes 14 has comb teeth parts 142.

The electrode base parts 131, 141 are formed on the accumulation section 10 along and in parallel to a longitudinal direction of the accumulation section 10. The comb teeth parts 132, 142 are formed extending from the electrode base parts 131, 141, in the first detection electrodes 13 and the second detection electrode 14 respectively. The first and second detection electrodes 13, 14 are arranged facing each other on the surface of the accumulation section 10, and the comb teeth parts 132, 142 are arranged alternately on the surface of the accumulation section 10 so that the comb teeth parts 142 in the second detection electrode 14 are arranged between the comb teeth parts 132 of the first detection electrodes 13.

Each of the comb teeth parts 132 has projecting parts 133, and each of the comb teeth parts 142 has projecting parts 143.

The projecting part 133, 143 has a mountain shape structure, a mountain-like shape structure, a triangle shape structure, or a triangle-like shape structure. The continuous formation of the projecting parts 133 and the projecting parts 143 provides the comb teeth parts 132 having a wave-like shape, and the comb teeth parts 142 having a wave-like shape. In the structure of the particulate matter detection sensor 100 according to the fourth exemplary embodiment, the minimum separation between the first detection electrode 13 and the second detection electrode 14 is 50 μm.

The fourth exemplary embodiment provides the particulate matter detection sensor 100 having a simpler structure.

In the particulate matter detection sensor 100 according to the fourth exemplary embodiment having the structure in which the first and second detection electrodes 13 and 14 having a plane film shape are formed on the surface of the accumulation section 10 by a by a pattern printing process, it is preferable that the minimum separation between the first detection electrode 13 and the second detection electrode 14 has a value of not less than 50 μm and is as small as possible. This structure makes it possible to provide the particulate matter detection sensor 100 with increased detection sensitivity because of having a reduced separation between the first and second detection electrodes 13, 14 while maintaining the production of those first and second detection electrodes 13, 14. Further, the particulate matter detection sensor 100 according to the fourth exemplary embodiment has the same behavior and effects as the particulate matter detection sensor 1 according to the first exemplary embodiment.

REFERENCE SIGNS LIST 1, 100 Particulate matter detection sensor, 10 Accumulation section, 11, 12, 13, 14 Detection electrode, 11, 13 First detection electrode, 12, 14 Second detection electrode, and 111, 121, 111-1, 121-1, 133, 143 Projection parts.

The invention claimed is:

1. A particulate matter detection sensor comprising:
an accumulation section which accumulates particulate matter particles contained in exhaust gas emitted from an internal combustion engine;
a detection electrode comprising a first detection electrode and a second detection electrode formed on the accumulation section, the second detection electrode being formed separated from the first detection electrode on the accumulation section,
wherein a plurality of projecting parts are successively formed along a first direction in the first detection electrode and/or the second detection electrode, and each of the plurality of projecting parts projects in a second direction which is perpendicular to the first direction, and the first detection electrode and the second detection electrode are not alternately formed in the first direction, and
a gap at each of the plurality of projecting parts formed between the first detection electrode and the second detection electrode is locally reduced at the projecting parts,
equipotential lines of electric field at each of the plurality of projecting parts have a high density when compared with equipotential lines of the electric field at an area not including the projecting parts between the first detection electrode and the second detection electrode.

2. The particulate matter detection sensor according to claim 1, wherein the plurality of projecting parts have one of a triangle-like shape and a trapezoid-like shape.

3. The particulate matter detection sensor according to claim 1, wherein the plurality of projecting parts are formed on both the first detection electrode and the second detection electrode, and
the plurality projecting parts are arranged so that the plurality of projecting parts formed in the first detection electrode and the plurality of projecting parts formed on the second detection electrode face each other.

4. The particulate matter detection sensor according to claim 3, wherein the plurality of projecting parts have one of a triangle-like shape and a trapezoid-like shape.

5. The particulate matter detection sensor according to claim 1, wherein a minimum separation between the first detection electrode and the second detection electrode is within a range of not less than 1 μm and not more than 50 μm.

6. The particulate matter detection sensor according to claim 5, wherein the plurality of projecting parts have one of a triangle-like shape and a trapezoid-like shape.

7. The particulate matter detection sensor according to claim 1, wherein
the first detection electrode, the second detection electrode and insulation members are alternately stacked in a stack direction in the particulate matter detection sensor, the insulation members have electric insulation properties, the detection electrode is sandwiched between the insulation members, the plurality of protruding parts are formed in the stack direction on a surface of one insulation member in the insulation members, and recess parts are formed on a surface of the other insulation member in the insulation members so that the projecting parts and the recess parts are alternately arranged in a direction which is perpendicular to the stacked direction.

8. A method of producing the particulate matter detection sensor according to claim 7 by alternately stacking the first detection electrode, the second detection electrode and the insulation members, and by joining the first detection electrode, the second detection electrode and the insulation members together, comprising the steps of:

stack each of the first detection electrode and the second detection electrode between a pair of the insulation members comprising a plurality of insulation projecting parts and a plurality of insulation depressed parts so as to face that the plurality of insulation projecting parts and the plurality of insulation depressed parts from each other; and press the pair of the pair of the insulation members and the first detection electrode, the second detection electrode together in a stacking direction of the insulation members so as to deform each of the first detection electrode, the second detection electrode sandwiched between the pair of the insulation members along the insulation projecting parts and the insulation depressed parts, and to form the plurality of projecting parts.

9. The particulate matter detection sensor according to claim 7, wherein the plurality of projecting parts have one of a triangle-like shape and a trapezoid-like shape.

\* \* \* \* \*